(12) United States Patent
Schilffarth

(10) Patent No.: US 8,570,512 B2
(45) Date of Patent: Oct. 29, 2013

(54) SYSTEM, STORAGE MEDIUMS, AND METHODS FOR IDENTIFYING PARTICLES IN FLOW

(75) Inventor: Adam Richard Schilffarth, Cedar Park, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 13/438,521

(22) Filed: Apr. 3, 2012

(65) Prior Publication Data
US 2012/0312085 A1 Dec. 13, 2012

Related U.S. Application Data

(62) Division of application No. 12/212,219, filed on Sep. 17, 2008, now Pat. No. 8,171,777.

(60) Provisional application No. 60/972,963, filed on Sep. 17, 2007.

(51) Int. Cl.
*G01N 15/14* (2006.01)
*G01N 15/02* (2006.01)
*G01N 21/53* (2006.01)
*G01N 21/64* (2006.01)

(52) U.S. Cl.
CPC ........ *G01N 15/1429* (2013.01); *G01N 15/1425* (2013.01); *G01N 15/1427* (2013.01); *G01N 15/1459* (2013.01); *G01N 15/0205* (2013.01); *G01N 2015/025* (2013.01); *G01N 2015/1438* (2013.01); *G01N 2015/1477* (2013.01)
USPC ....... 356/337; 73/865.5; 250/222.2; 250/565; 250/574; 250/575; 356/336; 356/341; 356/343; 702/28; 702/29

(58) Field of Classification Search
CPC .......... G01N 15/0205; G01N 15/0211; G01N 15/1425; G01N 15/1427; G01N 15/1429; G01N 15/1456; G01N 15/1459; G01N 21/53; G01N 21/64; G01N 21/85; G01N 2015/025; G01N 2015/1438; G01N 2015/1477; G01N 2021/4769
USPC ................... 73/865.5; 250/222.2, 458.1, 565, 250/574–575; 356/336–337, 341, 343, 951; 702/28–29
See application file for complete search history.

(56) References Cited

U.S. PATENT DOCUMENTS 4,765,737 A * 8/1988 Harris et al. ................... 356/336
5,682,038 A 10/1997 Hoffman ..................... 250/458.1
(Continued)

FOREIGN PATENT DOCUMENTS

DE 20104268 U1 * 6/2001 ............. G01N 15/14
EP 1 371 965 12/2003
(Continued)

OTHER PUBLICATIONS

Office Communication issued in Chinese Patent Application No. 200880107435.9, dated Oct. 26, 2011.
(Continued)

*Primary Examiner* — Thomas P Noland
(74) *Attorney, Agent, or Firm* — ParkerHighlander PLLC

(57) ABSTRACT

Methods, storage mediums, and systems for correlating pulses generated from multiple interrogation regions in a flow cytometer to particular particles flowing through the flow cytometer are provided. Embodiments of the methods, storage mediums, and systems include configurations for calibrating a flow cytometer using a calibration particle having a unique signature to determine a time-of-flight for particles flowing through the flow cytometer. Based on the calculated time-of-flight and relative positions of interrogation regions corresponding to collectors of the flow cytometer, the methods, storage mediums, and systems may further include configurations for associating other signal pulses to particles of one or more different particle sets.

8 Claims, 9 Drawing Sheets

(56) References Cited

U.S. PATENT DOCUMENTS

| | | |
|---|---|---|
| 5,760,900 A | 6/1998 | Ito et al. .................. 356/338 |
| 6,057,107 A | 5/2000 | Fulton .................. 435/6.12 |
| 6,268,222 B1 | 7/2001 | Chandler et al. .............. 436/523 |
| 6,449,562 B1 | 9/2002 | Chandler et al. ................ 702/19 |
| 6,514,295 B1 | 2/2003 | Chandler et al. .................. 8/607 |
| 6,524,793 B1 | 2/2003 | Chandler et al. .............. 435/6.12 |
| 6,528,165 B2 | 3/2003 | Chandler et al. ........... 428/402.2 |
| 6,592,822 B1 | 7/2003 | Chandler .................. 422/82.05 |
| 6,784,981 B1 * | 8/2004 | Roche et al. .............. 356/336 X |
| 6,906,792 B2 | 6/2005 | Ortyn et al. .................. 356/28.5 |
| 7,523,637 B2 | 4/2009 | Roth et al. .................. 73/1.02 |
| 7,691,636 B2 * | 4/2010 | Frazier et al. |
| 7,758,811 B2 | 7/2010 | Durack et al. .................. 422/73 |
| 7,776,268 B2 * | 8/2010 | Rich .................. 356/336 X |
| 7,981,682 B2 | 7/2011 | Evans .................. 436/63 |
| 8,149,402 B2 * | 4/2012 | Rich et al. .................. 356/343 |
| 8,253,938 B2 * | 8/2012 | Vacca et al. .................. 356/337 |
| 8,283,624 B2 * | 10/2012 | Antonov et al. .............. 250/281 |
| 2003/0142291 A1 | 7/2003 | Padmanabhan et al. ........ 356/39 |
| 2003/0228703 A1 | 12/2003 | Hoppe et al. .................. 436/172 |
| 2004/0053243 A1* | 3/2004 | Evans et al. .................. 435/2 X |
| 2004/0252304 A1* | 12/2004 | Goix et al. .................. 356/417 |
| 2005/0030519 A1 | 2/2005 | Roth .................. 356/28.5 |
| 2005/0106739 A1 | 5/2005 | Cabuz et al. .................. 436/63 |
| 2005/0282151 A1* | 12/2005 | Foster et al. .................. 435/4 |
| 2007/0064990 A1 | 3/2007 | Roth .................. 382/128 |
| 2007/0269814 A1* | 11/2007 | Wilkes et al. .................. 435/6 |
| 2008/0108146 A1 | 5/2008 | Jiang .................. 436/165 |
| 2009/0230324 A1 | 9/2009 | Gratton et al. ............. 250/459.1 |
| 2011/0024615 A1* | 2/2011 | Tanner et al. |
| 2013/0003049 A1* | 1/2013 | Matula et al. .................. 21/53 |

FOREIGN PATENT DOCUMENTS

| | | | |
|---|---|---|---|
| EP | 1 754 964 | 5/2007 | |
| WO | WO 9946047 A2 * | 9/1999 | ............. G01N 15/14 |
| WO | WO 0128700 A1 * | 4/2001 | ............. G01N 15/14 |
| WO | WO 0151007 A2 * | 7/2001 | ............. G01N 15/14 |
| WO | WO 2004106535 A2 * | 12/2004 | ............. G01N 15/14 |
| WO | WO 2005093784 A1 * | 10/2005 | ............. G01N 15/14 |
| WO | WO 2007051170 A2 * | 5/2007 | ............... C12M 3/00 |

OTHER PUBLICATIONS

Office Communication issued in European Patent Application No. 08 832 367.0, dated Jan. 21, 2011.

Office Communication issued in U.S. Appl. No. 12/212,219, dated Aug. 11, 2011.

Office Communication issued in U.S. Appl. No. 12/212,219, dated May 31, 2011.

PCT International Search Report and Written Opinion issued in International application No. PCT/US2008/076659, dated Dec. 17, 2008.

* cited by examiner

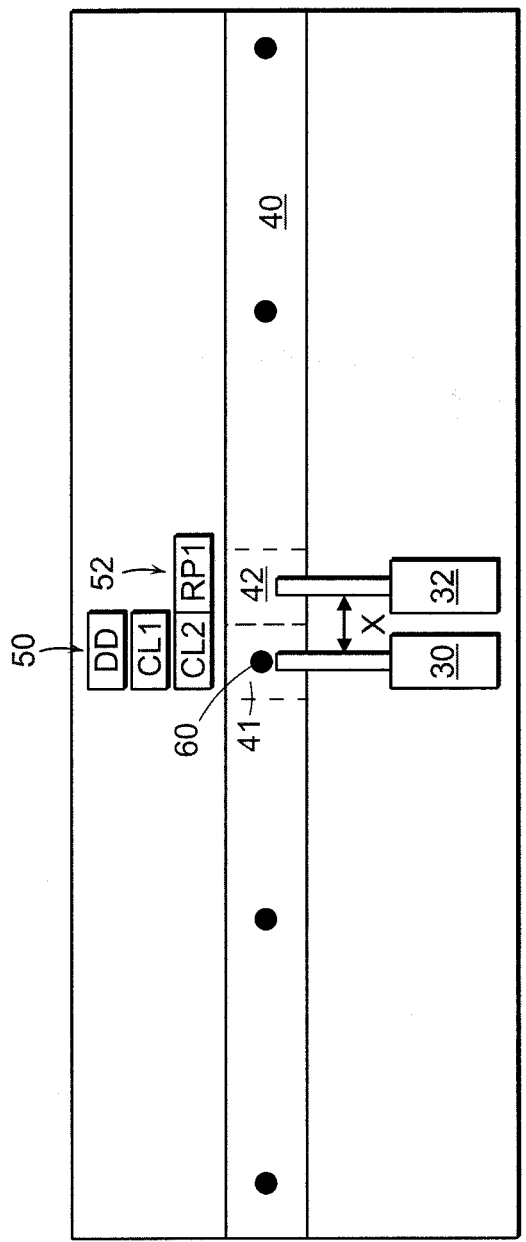

… (1)

SYSTEM, STORAGE MEDIUMS, AND METHODS FOR IDENTIFYING PARTICLES IN FLOW

PRIORITY CLAIM

The present application is a divisional application from U.S. patent application Ser. No. 12/212,219 filed Sep. 17, 2008, which claims priority to U.S. Provisional Patent Application No. 60/972,963 filed Sep. 17, 2007. U.S. patent application Ser. No. 12/212,219 and U.S. Provisional Patent Application No. 60/972,963 are incorporated herein by reference.

BACKGROUND OF THE INVENTION

1. Field of the Invention

This invention generally relates to flow cytometry systems, storage mediums, and methods and further relates to systems, storage mediums, and methods for interrogating and identifying particles flowing through a flow cytometer.

2. Description of the Related Art

Generally, flow cytometers provide measurements of fluorescent intensity of illuminated beads or particles as they pass linearly through a flow chamber. Two or more measurements of fluorescence may be used to classify particles to particular particle subsets. In addition, other fluorescence measurements known as "reporters" may be used to quantify chemical reactions of interest to determine the presence or absence of an analyte in an assay. Each of the fluorescent measurements is made at different wavelengths. In some cases, flow cytometers may further be used to provide measurements of one or more other properties of the particles, such as but not limited to the level of light scattered by a particle and/or the electrical impedance of a particle.

Many conventional flow cytometry measurement systems interrogate particles in two physical locations that are approximately 30 μm-100 μm apart along the direction of fluid flow. At the first interrogation point, a particle is illuminated with its scatter and fluorescence detected simultaneously on three channels, commonly referred to as "DD", "CL1", and "CL2". The same particle is then interrogated at a second point where illumination excites reporter tags that may be bound to the microsphere. This reporter fluorescence is detected on a channel commonly referred to as "RPI", but other references may be used. In such conventional flow cytometers, particle separation has been estimated to be approximately 400 μm-1,000 μm inside the flow cell. With the separation of particles being many times the distance between interrogation points, there is little chance of two particles being interrogated at two points simultaneously. As such, measurements consecutively collected at the two interrogation points are generally assigned to the same particle. However, as systems and/or techniques are employed where the probability of simultaneous interrogation of multiple particles at different interrogation points increases, accurately correlating pulses generated at different interrogation points within a flow cytometer presents a challenge.

SUMMARY OF THE INVENTION

The following description of various embodiments of methods, storage mediums, and systems for correlating pulses generated from multiple interrogation regions in a flow cytometer to particular particles flowing through the flow cytometer is not to be construed in any way as limiting the subject matter of the appended claims.

Embodiments of the methods, storage mediums, and systems include configurations for calibrating a flow cytometer using a calibration particle having a unique signature to determine a time-of-flight for particles flowing through the flow cytometer. Based on the calculated time-off-light and relative positions of interrogation points corresponding to collectors of the flow cytometer, the methods, storage mediums, and systems may further include configurations for associating other signal pulses to particles of one or more different particle sets.

BRIEF DESCRIPTION OF THE DRAWINGS

Other objects and advantages of the invention will become apparent upon reading the following detailed description and upon reference to the accompanying drawings in which:

FIG. 3 is a schematic diagram of components within a portion of an interrogation zone of a flow cytometer;

FIG. 4 is a schematic diagram of an alternative configuration of components within a portion of an interrogation zone of a flow cytometer;

Figure 1:
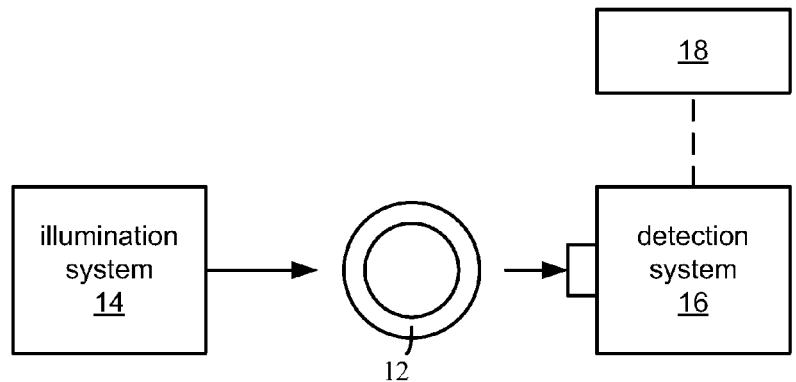
FIG. 1 is a schematic diagram of a flow cytometer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning to the drawings, exemplary methods, storage mediums, and systems for correlating pulses generated from multiple interrogation regions in a flow cytometer to particular particles flowing through the flow cytometer are provided. In particular, FIG. 1 illustrates a schematic diagram of an exemplary flow cytometer. In particular, FIG. 1 depicts flow cytometer 10 including flow system 12, illumination system 14, detection system 16, and controller 18. Flow system 12 may generally include a system configured to transport a fluid having a multitude of particles and further configured to focus the sample such that at least some of the particles may be individually interrogated. More specifically, flow system 12 may be configured to hydrodynamically focus an assay via a sheath fluid forming a particle flow path that allows particles to, for the most part, successively flow therethrough. In general, the entirety or a portion of such a particle flow path may serve as an interrogation zone in which multiple interrogation regions may be arranged to interrogate the particles. The methods, storage mediums, and systems described herein are applicable to any flow system where particles are serially interrogated and the term "flow cytometer" is intended to include all such systems. In addition, the methods, storage mediums, and systems described herein may be applied to flow cytometers for analyzing any type of assay, specifically any biological, chemical, or environmental assay in which determination of the presence or absence of one or more analytes of interest is desired.

The term "particle" is used herein to generally refer to microspheres, polystyrene beads, quantum dots, nanodots, nanoparticles, nanoshells, beads, microbeads, microparticles, latex particles, latex beads, fluorescent beads, fluorescent particles, colored particles, colored beads, tissue, cells, micro-organisms, organic matter, non-organic matter, or any other discrete substrates or substances known in the art. Any of such terms may be used interchangeably herein. In some cases, the particles may include materials that aid in identification, such as fluorescent, magnetic, electromagnetic resonant, and radioactive materials. Exemplary particles which may be used for the methods and systems described herein include xMAP® microspheres, which may be obtained commercially from Luminex Corporation of Austin, Tex. In general, the particles referenced herein may serve as vehicles for molecular reactions.

In general, illumination system 14 is configured to direct light toward multiple and distinct interrogation points of the particle flow path formed by flow system 12. The number of interrogation points may be any plurality of interrogation regions greater than one. As described in more detail below, in some cases it may be advantageous to have at least three interrogation points, but the systems and methods described herein are not so limited. In some embodiments, a different interrogation point may be used for each different parameter of the particles to be measured as described below in reference to FIG. 4. In other embodiments, however, more than one parameter may be measured at an interrogation point as described below in reference to the example illustrated in FIG. 3. In any case, the distance between the interrogation points are known, either by fixed known values or by inference of their relative spacing (i.e., equal or proportional spacing between the detectors). In this manner, a time-of-flight of a calibration particle may be determined and then applied to correlate pulses generated from multiple interrogation regions to particular particles of other particle subsets.

In general, illumination system 14 may include any number of light sources, including a single source of light or multiple sources of same type of light source or different types of light sources. In some embodiments, illumination system 14 may include a distinct light source for each interrogation point as shown in the exemplary systems shown in FIGS. 3 and 4 and described in more detail below. In such cases, the light sources may be arranged to directly project light toward the particle flow path of the flow cytometer and, thus, illumination system 14 may not necessarily include beamsplitters and reflecting mirrors to direct the light to the flow path. Such configurations may be advantageous for minimizing the size of the flow cytometer and/or simplifying the design of the flow cytometer. In other embodiments, beam splitters and reflecting mirrors may be included in an illumination system having a distinct light source for each interrogation point. In yet other cases, illumination system 14 may include a number of light sources less than a number of interrogation points the light sources are configured to direct light toward. In such embodiments, illumination system 14 may include beamsplitters and, in some cases, reflecting mirrors to direct the light from a single light source to multiple interrogation points. As such, although flow cytometer 10 shown in FIG. 1 and the exemplary configurations shown in FIGS. 3 and 4 are shown respectively directing light to flow system 12 and particle flow path 40 at a substantially normal angles of incidence, it is to be understood that illumination system 14 may be configured to direct light at any other suitable angle of incidence.

In any case, the light source/s of illumination system 14 may include any suitable light sources known in the art, such as but not limited to light emitting diodes (LEDs), lasers, arc lamps, fiber illuminators, light bulbs, and incandescent lamps. In addition, illumination system 14 may in some embodiments include optical components other than light sources, such as but 15 not limited to beamsplitters, reflecting mirrors, collimating lenses, spectral filters, neutral density filters, polarizing components, diffusers, and/or homogenizers. In some cases, illumination system 14 may be configured to sequentially illuminate particles with different wavelengths or wavelength bands of light (e.g., blue light and green light), such that the light directed to the particles is monochromatic, near monochromatic, polychromatic, or broadband. Furthermore, it is noted that the inclusion of illumination system 14 within flow cytometer 10 is optional and may generally depend on whether flow cytometer 10 is used for the detection of fluorescence emissions. In particular, flow cytometer 10 may in some embodiments be used to generate chemiluminescent reactions and measure resulting luminescent emissions, and in some cases may not be used to generate and measure fluorescent emissions. In such cases, illumination 25 system 14 may be turned off or omitted from flow cytometer 10.

As shown in FIG. 1, flow cytometer 10 may include detection system 16. In general, detection system 16 may be configured to collect light emitted and/or scattered from particles passing through interrogation regions of an interrogation zone of flow system 12. More specifically, detection system 16 may include a plurality of collectors configured to gather light from the interrogation regions and further configured to generate signals representative of a degree of light gathered. In particular, a collector's output current is proportional to the light impinging on it and results in a current pulse. The current pulse may be converted to a voltage pulse, low pass filtered, and then digitized by an analog/digital converter to produce a data signal. Depending on the light gathered, the data signal may be a scatter signal, report tag signal, fluorescence signal, magnetic signal, and/or electromagnetic resonance signal. It is noted that the function of the collectors of detection system 16 is described in reference to light gathered from interrogation regions rather than interrogation points. The term "interrogation point" as used herein refers to the point along a particle flow path that a light source is directed toward and illuminates. The term "interrogation region" as used herein refers to a region surrounding an interrogation point from which light may be gathered. In general, the area of an interrogation region may generally depend on the configuration of the collector used.

In general, detection system 16 may include a different collector for each different parameter of the particles to be measured. The collectors may include any type of photodetector, including but not limited to avalanche photodiodes (APD), photomultiplier tubes (PMT), charge coupled devices (CCD). In addition, the collectors may be of the same type or of different types, depending on the type of light to be gathered. In some cases, detection system 16 may include filters, mirrors, and/or lenses. In some embodiments, collectors of detection system 16 may be configured to gather light from different interrogation regions of an interrogation zone as shown in the exemplary system shown in FIG. 4 and described in more detail below. In such cases, the collectors may be arranged to gather light directly from the interrogation regions and, thus, detection system 16 may not necessarily include beamsplitters and reflecting mirrors to gather the light to the different collectors. Such configurations may be advantageous for minimizing the size of the flow cytometer and/or simplifying the design of the flow cytometer. In other embodiments, beam splitters and reflecting mirrors may be included in a detection system having a collector for each distinct interrogation region.

In other cases, some of the collectors of detection system 16 may be configured to gather light from the same interrogation region as shown in the exemplary system shown in FIG. 3 and described in more detail below. In such embodiments, detection system 16 may include beamsplitters and, in some cases, reflecting mirrors to direct the light from the interrogation region to the multiple collectors. Such additional elements are not shown in FIG. 3 to simplify the drawing and, thus, are not to be construed as being omitted. As such, although flow cytometer 10 shown in FIG. 1 and the exemplary configurations shown in FIGS. 3 and 4 are shown respectively gathering light at substantially normal angles of incidence, it is to be 5 understood that detection system 16 may be configured to gather light at any other suitable angle.

Figure 2:
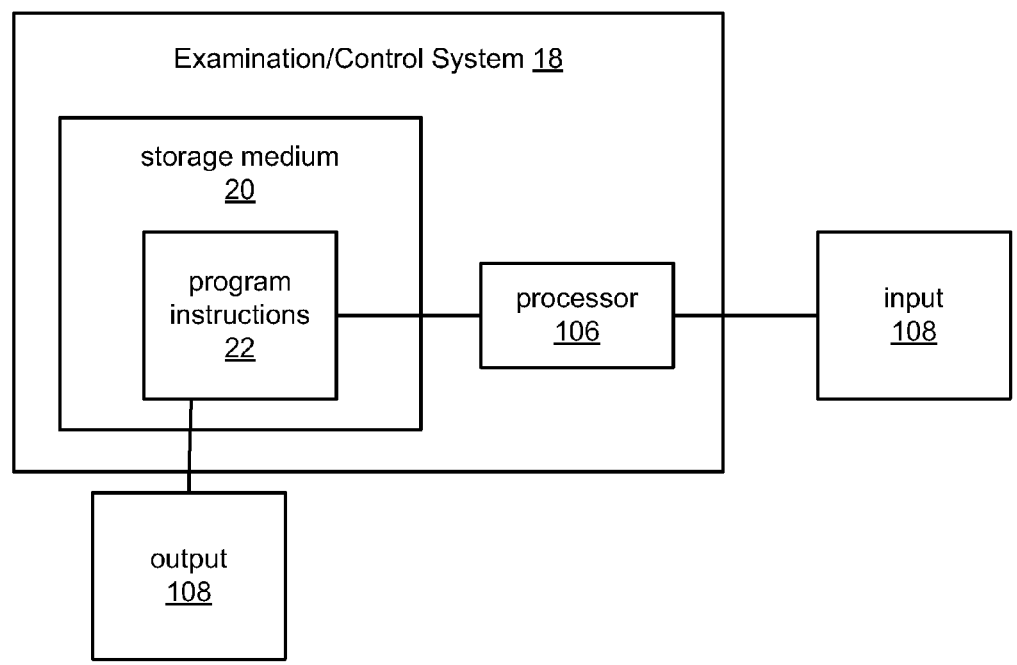
FIG. 2 is a schematic diagram of an exemplary examination system for the flow cytometer depicted in FIG. 1.

As further shown in FIG. 1, flow cytometer 10 may include examination system 18 operatively coupled to detection system 16. In general, examination system 18 may be configured to receive, monitor, and evaluate signals generated from the collectors of the detection system such that the types and/or amount of analytes within a sample may be ascertained. In some embodiments, examination system 18 may be part of a control system which is configured to automate the operations of flow cytometer 10. In such cases, examination system 18 may be further operatively coupled to flow system 12 and illumination system 14. In other embodiments, examination system 18 may be separate from such a control system. In 15 either case, examination system 18 may include a processor and program instructions which are executable by the processor for performing any of the processes described in the flow charts outlined in FIGS. 9-11 as well as the graphs depicted in FIGS. 5-8. A schematic diagram of an exemplary configuration for examination system 18 is shown in FIG. 2. It is noted that such a configuration is merely exemplary and, thus, other configurations may be considered.

As shown in FIG. 2, examination system 18 includes storage medium 20 and processor 24. Examination system 18 may take various forms, including a personal computer system, mainframe computer system, workstation, network appliance, Internet appliance, personal digital assistant (PDA), a digital signal processor (DSP), field programmable gate array (FPGA), or other device. In any case, storage medium 20 includes program instructions 2224 which are executable using processor 24 for generating and transmitting output 28. As described in more detail below, examination system 18 is configured to receive input 28 (i.e., signals generated from collectors of detection system 16) to activate program instructions 22 though processor 24 and/or contribute data for program instructions 22 to process. Although not shown in FIG. 2, storage medium 20 may include databases and/or look-up tables which program instructions 22 may access for performing the processes outlined below. Exemplary databases and/or look-up tables may include, for example, predetermined signal ranges and/or threshold values by which to compare signals received from detection system 16. In other embodiments, such predetermined signal ranges and/or threshold values may be included in program instructions 22 and, thus, the databases and/or look-up tables may be omitted from storage medium 20.

In general, the term "storage medium", as used herein, may refer to any electronic medium configured to hold one or more set of program instructions, such as but not limited to a read-only memory, a random access memory, a magnetic or optical disk, or magnetic tape. The term "program instructions" may generally refer to commands within a program which are configured to perform a particular function, such as correlating pulses generated from multiple interrogation regions in a flow cytometer to particular particles flowing through the flow cytometer as described in more detail below. Program instructions may be implemented in any of various ways, including procedure-based techniques, component-based techniques, and/or object oriented techniques, among others. For example, the program instructions may be implemented using ActiveX controls, C++ objects, JavaBeans, Microsoft Foundation Classes ("MFC"), or other technologies or methodologies, as desired. As noted above, program instructions 24 may be generally configured to perform the processes outlined in the flowcharts depicted in FIGS. 59-11. As such, the flowcharts depicted in FIGS. 9-11 generally describe methods carried out through the use of a software module. More specifically, the methods described in reference to FIGS. 9-11 include analyzing and computing a relatively large amount of data through the use of one or more algorithms and, therefore, may be best implemented through a computer. Consequently, the methods described in reference to FIGS. 9-11 may be referred to as "computer-implemented methods."

FIGS. 3 and 4 depict portions of exemplary interrogation zones of flow cytometers which may be considered for the methods and systems described herein. In particular, FIGS. 3 and 4 illustrate schematic drawings of exemplary portions of flow cytometers in which the positions of light sources of illuminations systems and collecting devices of detection systems are shown relative to a particle flow path of the flow cytometers. It is noted that the illustrations of FIGS. 3 and 4 are exemplary and are not to be construed to limit the configurations of flow cytometers considered for the methods and systems described herein. Rather, FIGS. 3 and 4 are merely used to describe some possible arrangements of flow cytometer components and further to aid in describing the process steps described in reference to FIGS. 5-12.

As shown in FIG. 3, illumination system 14 may in some embodiments include two light sources, namely light sources 30 and 32, directed at two distinct interrogation points within interrogation regions 41 and 42 of particle flow path 40. On the receiving end of interrogation regions 41 and 42 is collector set 50 and collector 52, respectively. As shown in FIG. 3, collector set 50 includes three collectors, one for each of channels DD, CL1, and CL2. In this manner, scatter and fluorescence emitted from a single passing particle, such as particle 60 denoted in FIG. 3, may be detected simultaneously. In some cases, such channels may be used to classify particle 60 to a particular particle set. Thereafter, particle 60 will pass through interrogation region 42 such that light may be collected by collector 52 which may include a reporter tag channel (denoted as "RP1" in FIG. 3). The reporter tag channel may generally be used to detect and/or quantify an amount of analyte on a passing particle.

As noted above, the interrogation points of interrogation regions 41 and 42 are dependent on the incidence of light from light sources 30 and 32 and, thus, the separation between the interrogation points of the regions is denoted by spacing X as shown in FIG. 3. In general, the distance of spacing X and the separation of the particles denoted in FIG. 3 is such that simultaneous interrogations at different interrogation points are unlikely. In particular, the interrogation points are so close to each other (e.g., approximately 30 µm-100 µm) that particle separation in the passing fluid (e.g., a particle separation of approximately 400 µm-1,000 µm) is much greater than spacing X, making simultaneous particle interrogations at multiple interrogation points unlikely. As noted above, such interrogation zone configurations are common in conventional flow cytometers. It is noted, however, as the need for greater particle concentration within assays continues, such configurations may eventually succumb to scenarios in which particle separation in the passing fluid is equal to or less than spacing X, making simultaneous particle interrogations at different interrogation points likely. In particular, particle separation within passing fluids may decrease to less than approximately 100 µm at some point in the near future. As such, it is contemplated that the methods and systems described herein may be applicable to configurations of flow cytometers described in FIG. 3 as well as any other configurations of flow cytometers.

FIG. 4 illustrates an alternative embodiment of an interrogation zone of a flow cytometer. In particular, FIG. 4 depicts illumination system 14 including light sources 34, 36, 38, and 32 directed at distinct interrogation points of interrogation regions 45-48 of particle flow path 44. On the receiving end of interrogation regions 45-48 are collectors 54, 56, 58, and 52, respectively. More specifically, interrogation region 45 is associated with light source 34 and collector 54 comprising channel DD. Interrogation region 46 is associated with light source 36 and collector 56 comprising channel CL1 and interrogation region 47 is associated with light source 38 and collector 58 comprising channel CL2. Likewise, interrogation region 48 is associated with light source 32 and associated collector 52 comprising channel RP1. In contrast to FIG. 3, FIG. 4 illustrates a portion of an interrogation zone of a flow cytometer in which the particle separation is equal to or less than interrogation point separation (denoted as spacing Y in FIG. 4), making simultaneous particle interrogations at multiple interrogation points likely. In the illustrative embodiment of FIG. 4, simultaneous interrogations are occurring at regions 45, 46, and 47. Closely spaced particles relative to interrogation point separation can result from a variety of conditions, such as closely spaced beads, large numbers of beads, or wide separation of interrogation points. As described above, the number of interrogation points, spacing, and excitation sources can be varied without departing from the scope of the methods and systems described herein.

Figure 5:
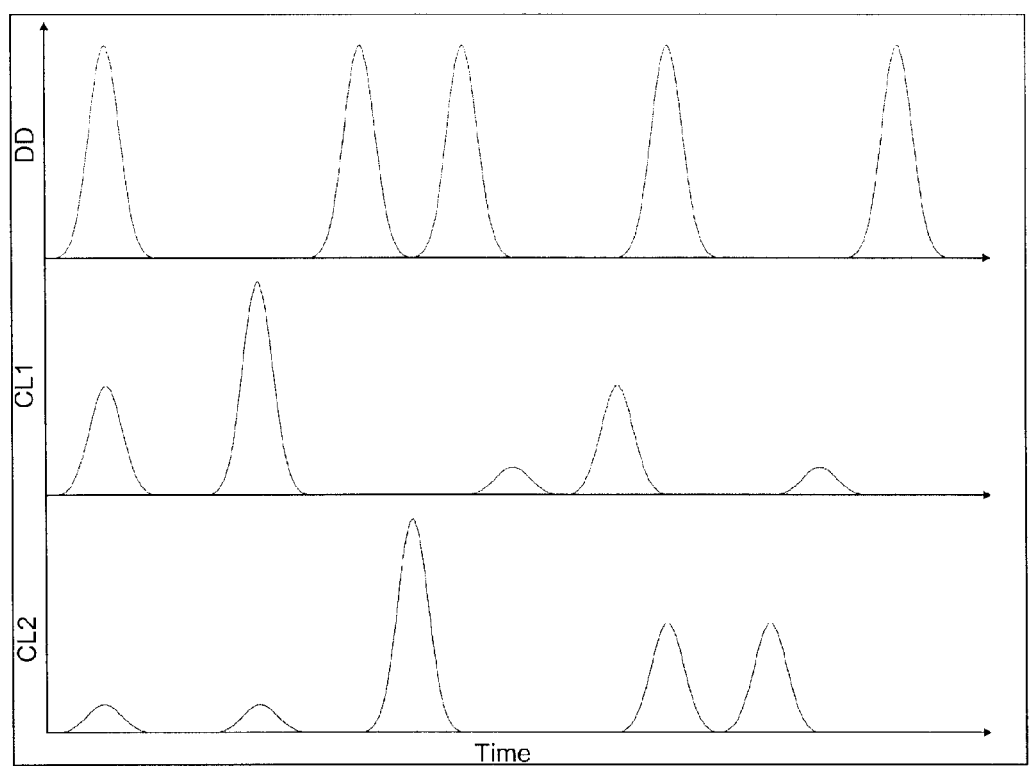
FIG. 5 is a graph plotting waveforms from generated from channels DD, CL1, and CL2 of a detection system of a flow cytometer.
Figure 8:
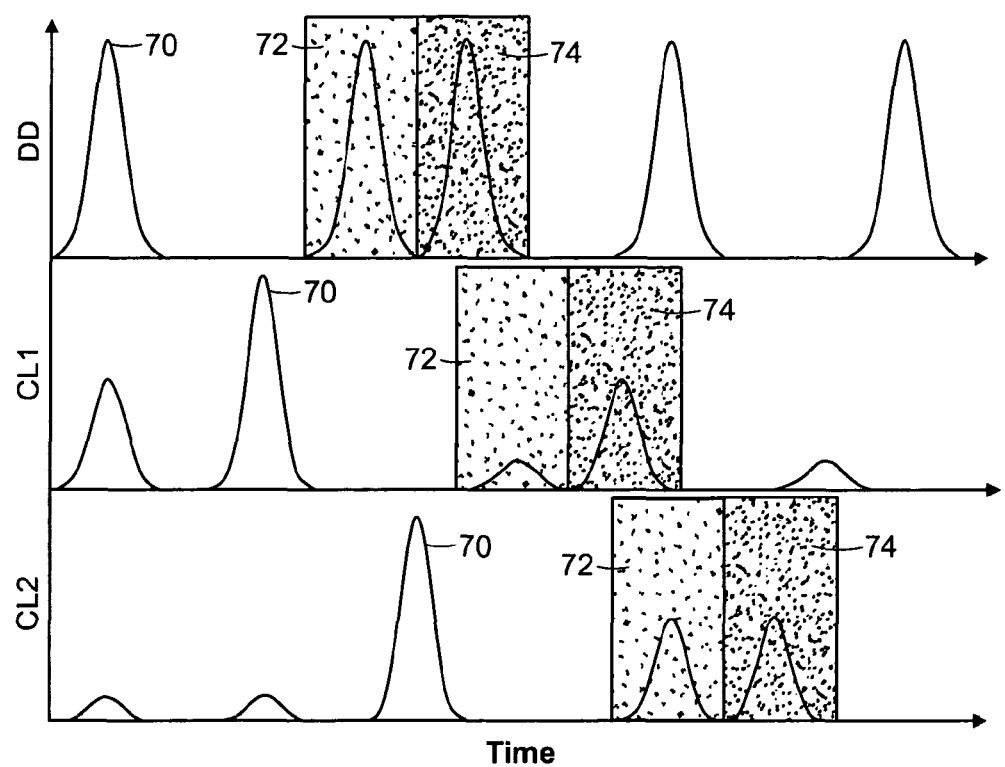
FIG. 8 is a waveform graph similar to FIG. 5 with the pulses on individual channels assigned to common particles.
Figure 9:
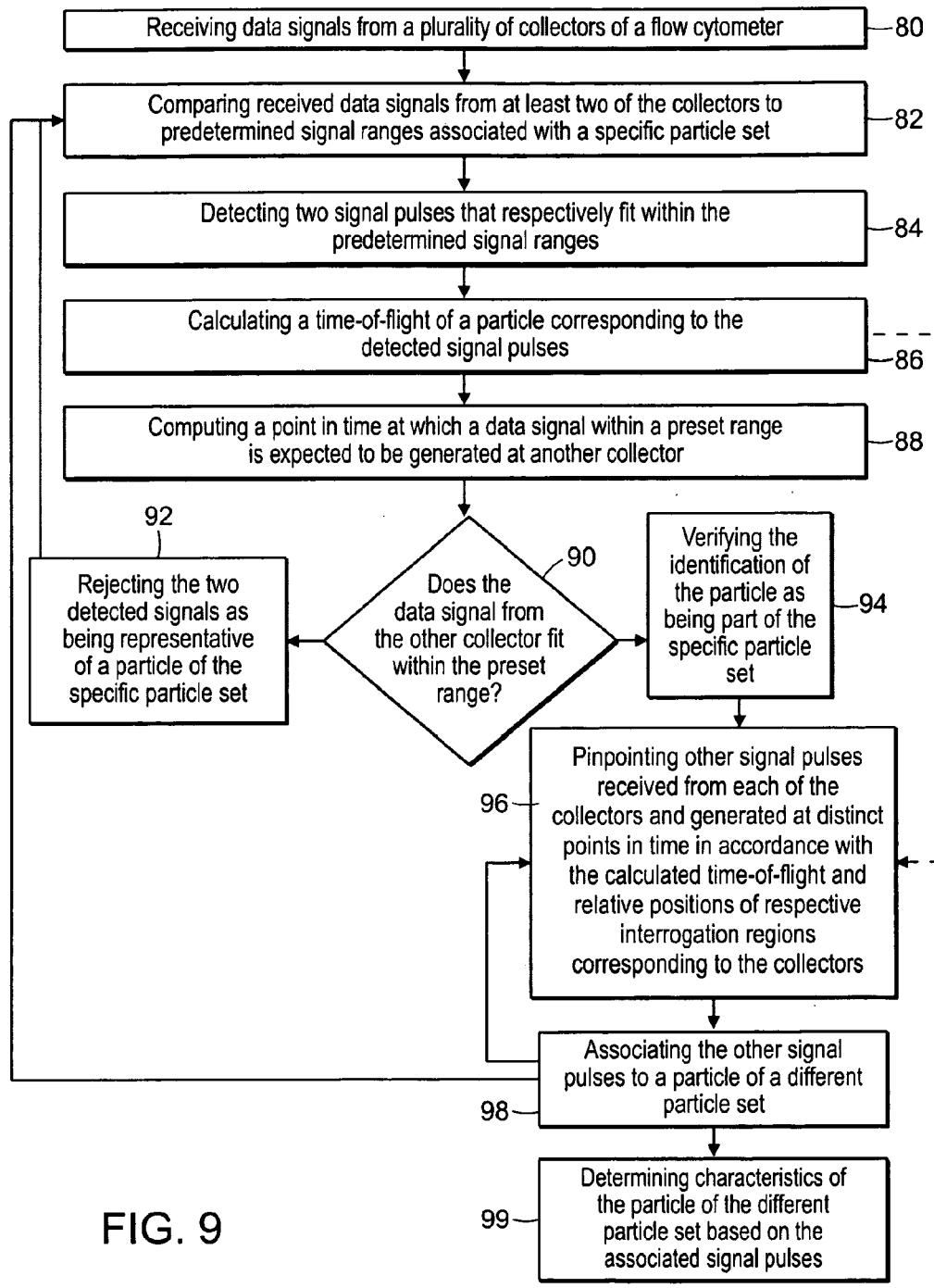
FIG. 9 is a flow chart of processes for correlating signal pulses generated from multiple interrogation regions in a flow cytometer to particles of distinct particle subsets in an assay.
Figure 10:
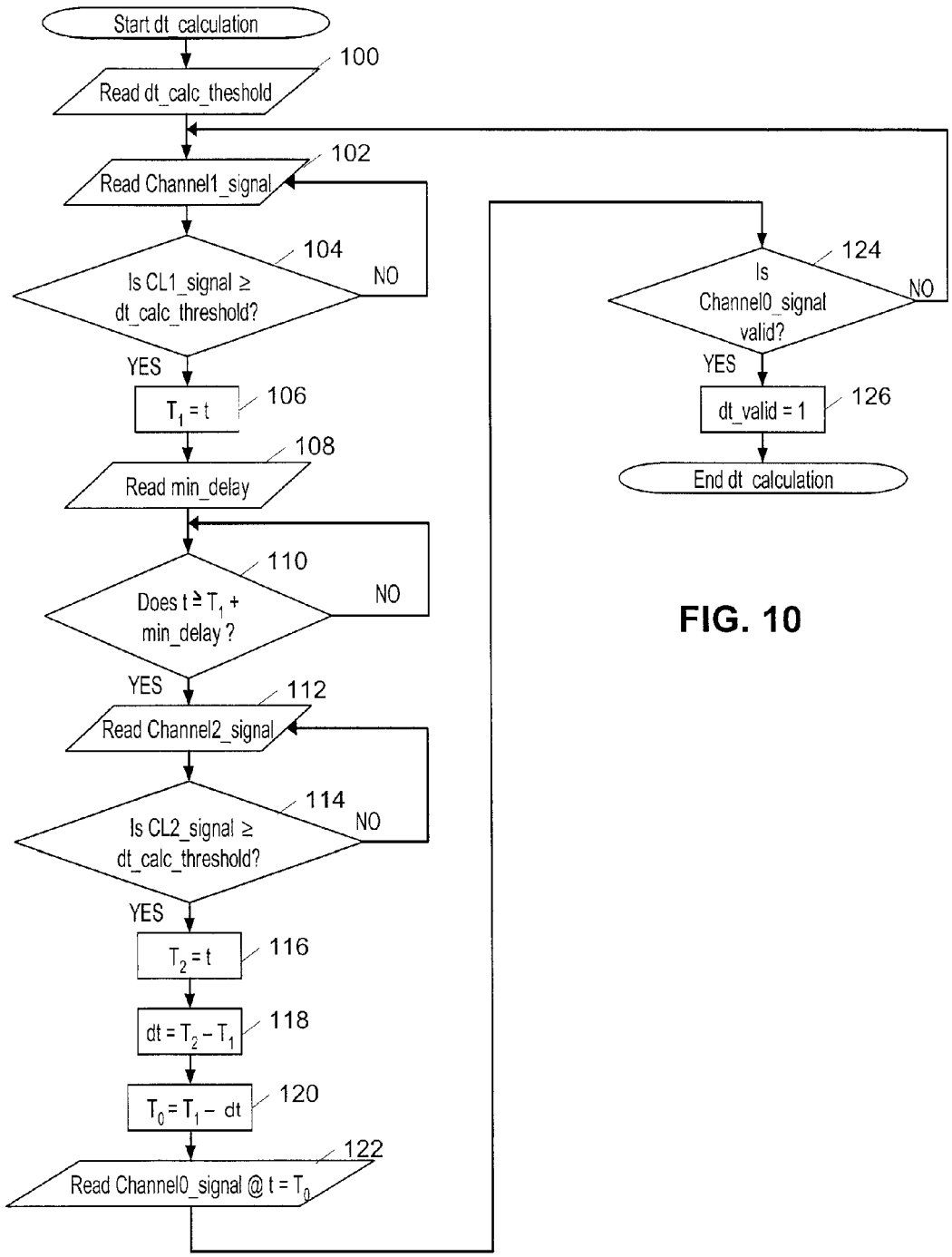
FIG. 10 is a flow chart of a process for calibrating a flow cytometer to determine a time-of-flight of particles flowing through the flow cytometer.
Figure 11:
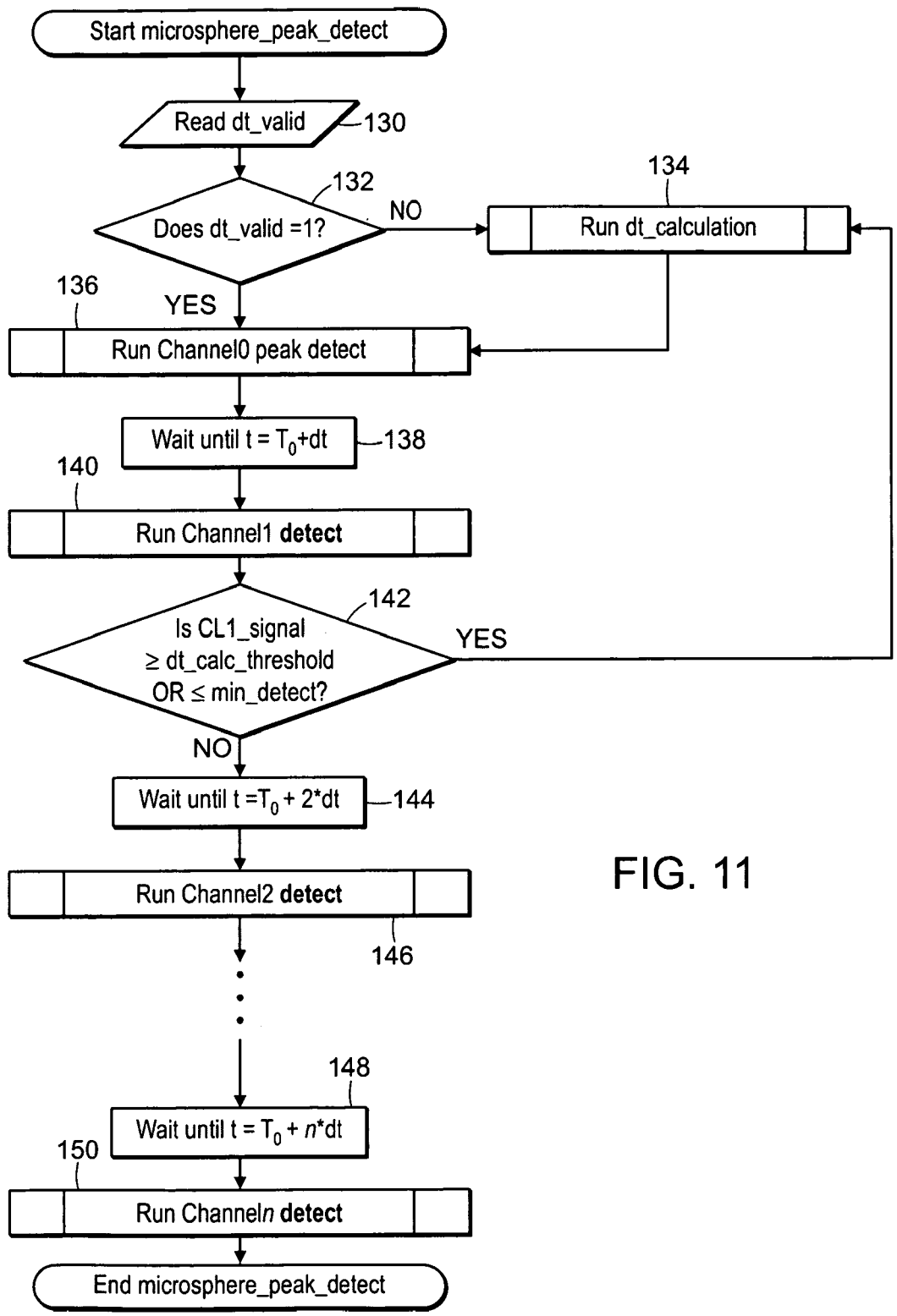
FIG. 11 is a flow chart of a process for correlating pulses generated at different interrogation points of a flow cytometer.

FIG. 5 shows hypothetical waveforms on the DD, CL1, and CL2 channels associated with the three interrogation windows 45-47 of FIG. 4. As can be seen in FIG. 5, there are multiple simultaneous waveform pulses between the three channels. To classify a particle flowing through the interrogation zone, it must be known which pulses belong to a given particle. The methods and systems described herein correlate a particle to a pulse using processes which use: 1) known interrogation point locations; 2) uniquely identifiable particles for time-of-flight calculations; and 3) detection algorithms. An example employing such processes in described below in reference to FIGS. 4-8. Thereafter, the flow charts depicted in FIGS. 9-11 are described delineating a fuller scope of the processes.

In general, the methods and systems described herein function by identifying unique signals associated with a "calibration" particle on at least two channels. These unique signals can include, but are not limited to unique scatter signal due to size, a unique reporter tag signal, one or more unique signals due to dyes, a unique magnetic signature, unique electromagnetic resonance, or radioactivity. The example presented below in reference to FIGS. 4-7 utilizes two consecutive channels but any channels with a known separation will work. In some embodiments, it may be advantageous to employ channels having a relatively large separation. In particular, larger separations offer greater error tolerances in calculating a time-of-flight of a particle. Thus, in some embodiments, it may be desirable to employ channels on either end of an interrogation zone for the identification of a calibration particle.

Figure 6:
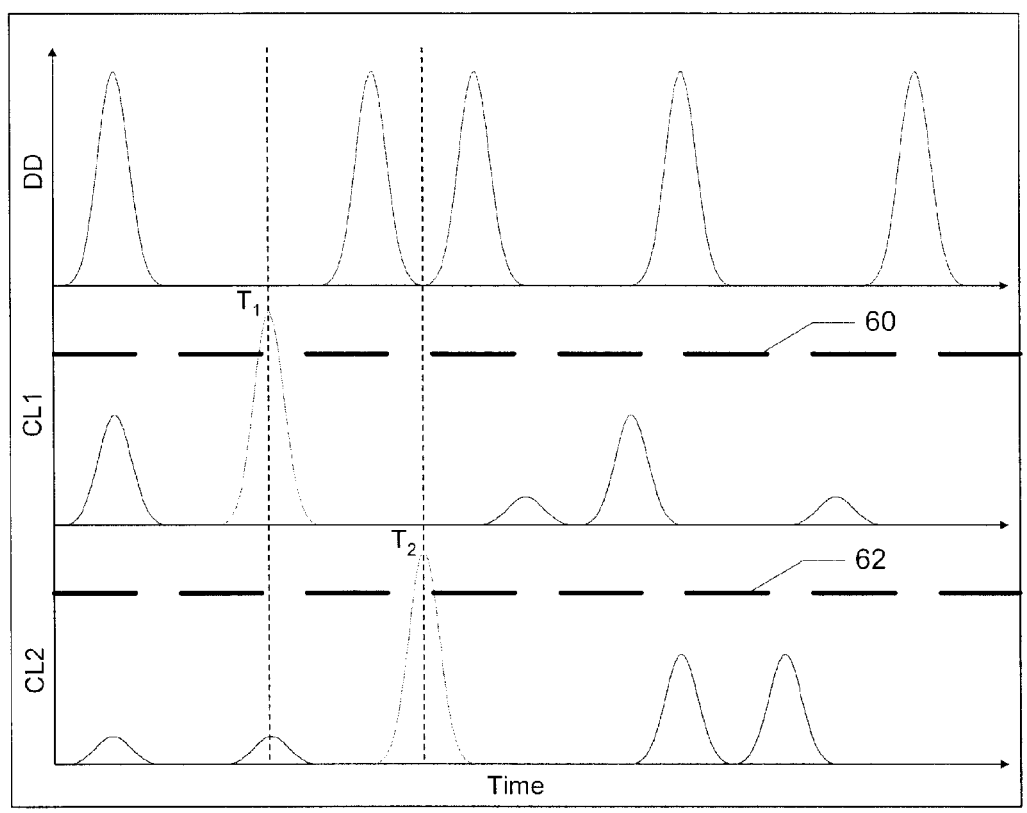
FIG. 6 is a waveform graph similar to FIG. 5 with a time-of-flight calibration particle threshold overlaid.

In general, a calibration particle subset may have a unique range of signal values difference than other particle subsets within the assay. In some embodiments, a calibration particle subset may have unique signals in the form of higher signals than all other particle subsets within the assay. FIG. 6 illustrates such an embodiment. In particular, FIG. 6 shows the waveforms from FIG. 5 with calibration particle identification thresholds 60 and 62 shown for channels CL1 and CL2, respectively. It is noted that one or more alternative or additional channels may be used for the detection of a calibration particle and, thus, the methods and systems described herein should not be limited to the example described in reference to FIG. 6. In particular, it is to be understood that the embodiments described herein may use any measurable parameter of particles that can be used to distinguish different populations of the particles.

As shown in FIG. 6, the location on the time axis of the pulse peaks that cross the identification thresholds on CL1 and CL2 are marked as $T_1$ and $T_2$, respectively. The time difference between such pulses, denoted as dt, can be found by:

$$dt = T_2 - T_1$$

It is possible that the threshold crossing signals on CL1 and CL2 could have been due to an aggregate of particles. As such, in some embodiments, it may be advantageous to verify a single calibration particle has indeed been identified. To answer this question, the DD channel may be looked at for a signal that falls within acceptable limits. The DD channel examines at scatter off of the particle to determine whether a single particle or an aggregate of multiple particles was discovered. In the embodiments described in reference to FIGS. 4-7, the DD channel is positioned upstream and adjacent to CL1 channel. In such cases, the position of DD channel signal, $T_0$, corresponding to the particle can be found by:

$$T_0 = T_1 - dt$$

It is noted, however, that such a calculation may change depending on the position of the DD channel relative to the channels used to detect the calibration particle (e.g., CL1 and CL2).

Figure 7:
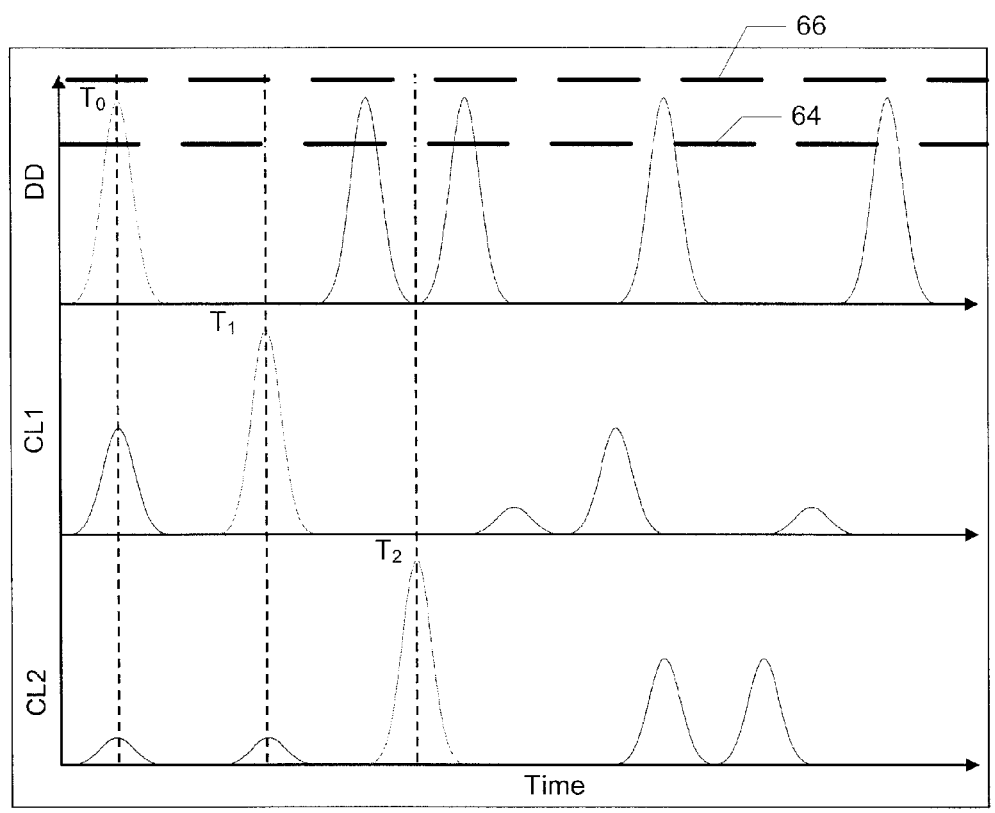
FIG. 7 is a waveform graph similar to FIG. 5 with the DD channel high and low signal thresholds marked.

FIG. 7 is the waveform from FIG. 5 showing the DD signal level bounds 64 and 66 as well as the identification of pulse peaks $T_0$, $T_1$, and $T_2$ on DD, CL1, and CL2 channels, respectively. As shown in FIG. 7, the DD channel pulse at $T_0$ falls within the acceptable limits, i.e. it is between bounds 64 and 66, so the detection of a time-of-flight calibration particle has been confirmed. Particles can now be extracted from the DD, CL1, and CL2 signals as shown in FIG. 8. In FIG. 8, a first particle is associated with a series of consecutive signal pulses on channels DD, CL1, and CL2 as denoted by reference number 70. A second particle is associated with a different series of pulses on the channels and is denoted by reference number 72, and a third particle is associated with yet another series of pulses on the channels and is denoted by reference number 74. Each of such series of signal pulses are in accordance with the time-off-light previously calculated for a calibration particle passing through the flow cytometer and the relative position of the interrogation points associated with the respective collecting devices comprising channels DD, CL1, and CL2. In the illustrated embodiment, the process requires buffering the DD channel signal since the $T_0$ time point will occur before a calibration particle signal triggers the time-of-flight calculation process.

It is believed that in many cases the particle velocities through a flow cytometer will vary enough to justify frequent recalibration. In such cases, time-of-flight calibration particles are mixed into a sample in sufficient quantities to other particles to ensure the time-of-flight calibration is done many times in a given period of time (such as many times a second) ensuring that any perturbations in particle velocity are accounted for. If a new time-of-flight calibration particle is detected then dt is recalculated and updated with the new value and subsequent microspheres identified with the new value.

Flowcharts outlining a fuller scope of the processes which may be employed by the methods and systems described herein are shown in FIGS. 9-11. In particular, FIG. 9 illustrates general processes employed for detecting and determining a time-of-flight for a calibration particle as well as subsequently pinpointing and assigning signal pulses based on the calculated time-of-flight and relative position of interrogation points within the flow cytometer. FIG. 10 illustrates an exemplary set of instructions which may be used to perform the calibration process. FIG. 11 illustrates an exemplary set of instructions which may be used to correlate pulses generated from multiple interrogation regions to particular particles based on the calibration process described in reference to FIG. 10. It is noted that the methods and systems described herein are not necessarily restricted to the processes described in reference to FIGS. 9-11. In particular, the processes may in some embodiments, include additional steps which are not depicted in the flowcharts. In addition, as noted below, one or more of the processes described in reference to FIGS. 9-11 may be optional and, therefore, may be omitted in some embodiments.

As shown in block 80 of FIG. 9, the methods and systems described herein may be configured to receive data signals from a plurality of collectors of a flow cytometer. In addition, the methods and systems described herein may be configured to compare received signals of at least two collectors to predetermined signal ranges associated with a specific particle set (i.e., a calibration particle set) as set forth in block 82. In some cases, signals which are not associated with a parameter for detecting a calibration particle may be essentially ignored at this point. More specifically, the signals need not be monitored, much less stored in memory. Such a scenario may aid in reducing processing and/or memory requirements of the examination system for the flow cytometer. In other embodiments, the signals not associated with a parameter for detecting a calibration particle may be monitored and/or stored.

In either case, upon detecting signal pulses that respectively fit within the predetermined signal ranges associated with the calibration particle set, a time-of flight of a particle corresponding to the two detected signals is calculated as respectively noted in blocks 84 and 86 of FIG. 9. As used herein, the term "time-of-flight" may generally refer to the time it takes a particle to travel a known distance, such as between two interrogation points of a flow cytometer. In some embodiments, a time-of-flight may merely include a time difference between signal pulses received from two detectors. In such cases, the known distances between the interrogation points corresponding to the detectors is either inferred by equal spacing between all detectors of a flow cytometer or by known proportional spacing between the detectors of the flow cytometer. In the latter embodiments, "known proportional spacing" may generally refer to the distances between consecutively arranged interrogation points being proportional to each other. For example, in reference FIG. 4, the spacing between collectors 58 and 52 is denoted by distance Y. Instead of being equally spaced throughout particle flow path 44, collectors 54 and 56 may be spaced proportionally relative distance Y. For instance, collector 56 may be spaced a distance ½Y from collector 58 and collector 54 may be spaced a distance 2Y from collector 56. Other proportional distances may also be considered and, thus, the methods and systems described herein are not restricted to the aforementioned example.

In yet other cases, a time-of-flight may include a velocity of a particle. In such embodiments, the distance between each of the detectors is a known fixed value, regardless of whether the distances between each of the detectors are the same or different. Calculating the velocity of a particle may be particularly applicable (but not necessarily limited to) when interrogation points are not evenly distributed throughout an interrogation zone of a flow cytometer and/or when the interrogation points in question are not consecutively arranged within an interrogation zone of a flow cytometer.

In some cases, the detection of the signal pulses in block 84 may include specifically identifying the particle corresponding to the two detected signals as a particle of the specific particle set. In such cases, the method may follow one of two routes, one being to determine whether the particle is indeed part of the specific particle set as outlined in blocks 88-94 and the other skipping such processes and routing the method directly to blocks 96 and 98 to assign other signal pulses to a particle of a different particle set. FIG. 9 includes a dotted lined between blocks 86 and 96 denoted the latter embodiment as an alternative option. In view of both options, the processes outlined in blocks 82-86 and the processes outlined in block 82-94 may each be referred to as calibrating a flow cytometer using a calibration particle having a unique signature to determine a time-of-flight for particles flowing through the flow cytometer. Advantages for selecting each option are described in more detail below.

Due the susceptibility of particle clumping in an assay, it is possible that the two signals detected in reference to block 84 are due to an aggregate of particles rather than a single particle of a calibration particle set. It is postulated that depending on the flow rate of the particles in a flow cytometer and the separation distances between interrogation points of a flow cytometer, the differences of speed between an aggregate of particles and a single particle may be appreciably similar and, thus, a time-of-flight for an aggregate of particles may be applicable for correlating pulses generated from multiple interrogation regions to particular particles. As such, in some embodiments, the method may continue directly to blocks 96 and 98 to assign other signal pulses to a particle of a different particle set, regardless of whether a calibration particle or an aggregate of particles has been detected. Such an option may avoid the extra step of verifying the detection at another collector (a process which is described in more detail below in reference to blocks 88-94) and, thus, may simplify the program instructions for the methods and systems described herein.

It is also theorized that, in other embodiments (generally cases in which relatively higher flow rates of particles and/or narrower separation distances between interrogation points are employed), the differences of speed between an aggregate of particles and a single particle may be significantly different. In such cases, an inaccurate time-of-flight may be calculated from an aggregate of particles and correlating pulses therefrom may not be feasible. As such, it may, in some embodiments, be advantageous to verify whether the two signals detected in reference to block 84 is indeed a single calibration particle. In such cases, the process outlined in FIG. 9 routes to block 88 to compute a point in time at which a data signal within a different predetermined range is expected to be generated at another collector based upon the detection of the two data signals and calculated time-of-flight described in reference to block 86. In particular, the time is computed in accordance with the calculated time of flight and a position of an interrogation point corresponding to the other collector relative to positions of the interrogation points corresponding to the two collectors. Such a time computation may be for an interrogation point positioned either upstream or downstream relative to the two or more interrogation points used to identify the calibration particle. In cases in which the time is computed for an interrogation point positioned upstream, the methods and systems described herein may be configured to store the signal associated with the other interrogation point and then reference the stored signal subsequent to interrogating the calibration particle at the two or more interrogation points to confirm the identification of the calibration particle.

In any case, the collector used for the verification process may include any channel configured to generate signals which differentiate between single particles and clumps of particles. A collector configured to generate signals based on light scattered from the matter being analyzed (such as a DD channel) is a viable option, since scattered light is generally indicative of matter size. As shown in block 90 in FIG. 9, a determination is made as to whether the data signal from the other collector fits within the preset signal range. As shown in block 92, the two detected data signals are rejected as being representative of a particle of the specific particle set (i.e., a calibration particle) upon determining the data signal collected from the other collector is not within the different preset range and the process is routed back to block 82 to continue to compare receive data signals to predetermined signal ranges associated with the specific particle set. However, upon determining the data signal collected from the other collector is within the different preset range, the identification of the particle as being part of the specific particle set is verified as shown in block 94.

FIG. 10 illustrates an exemplary flow chart for calibrating a flow cytometer, specifically identifying a calibration particle, calculating a time-of-flight of the calibration particle, and verifying the calibration particle is a single particle rather than a clump of particles. It is noted that FIG. 10 is exemplary and, thus, other manners of carrying out the processes outlined in blocks 80-84 of FIG. 9 may be employed. For instance, FIG. 10 specifically calls for computing a time difference (dt) for calculating a time-of-flight of a particle. As noted above, however, calculating a time-of-flight may alternatively include computing a velocity of a particle. Other variations to the instructions noted in FIG. 10 may be also or alternatively employed based on the discussions noted above. As shown in FIG. 10, the calibration process includes block 100 at which dt_calc_threshold is read. Correlating such a process to block 82 of FIG. 9, parameter "dt_calc_threshold" refers to the predetermined signal ranges associated with the calibration set specific to the two or more channels used to calibrate the flow cytometer. For the embodiment outlined in FIG. 10, signals from two channels (referenced as Channel1 and Channel2) are compared to the values of dt_calc_threshold.

As noted in blocks 102 and 104 in FIG. 10, a signal from Channel1 is read and compared to dt_calc_threshold for that channel. If the signal from Channel1 is less than dt_calc_threshold for that channel, the process is routed back to block 102 to continue to monitor signals from Channel1. However, when the signal from Channel1 is greater than or equal to dt_calc_threshold for that channel, the process continues to block 106 to assign the timing of the signal (i.e., current time t) to variable $T_1$. Thereafter, a minimum time delay (min_delay) is read at block 108 and at block 110 a determination is made regarding whether current time t is equal to or greater than $T_1$+the minimum time delay. In general, the minimum time delay represents the minimum amount of time expected to occur between interrogation points based on the anticipated flow rate of the fluid through the flow cytometer and the spacing of the interrogation points. Consideration of such a delay aids in preventing detection of different calibration particles which may be flowing in succession between interrogation points, which may lead to calculating a false time-of-flight. As noted in FIG. 10, if current time t does not equal to or is not greater than $T_1$+the minimum time delay, then the process is routed back to block 110 until such a determination is made.

Thereafter, a signal generated from Channel2 is read at block 112. As with blocks 104 and 106 for Channel1, the signal generated from Channel2 is read and compared to dt_calc_threshold for that channel at blocks 112 and 114, respectively. If the signal from Channel2 is less than dt_calc_threshold for that channel, the process is routed back to block 112 to continue to monitor signals from Channel2. However, when the signal from Channel2 is greater than or equal to dt_calc_threshold for that channel, the process continues to block 116 to assign the timing of the signal (i.e., current time t) to variable T2. Thereafter, a time difference (dt) between the timings of the signals is generated at block 118. Then, at block 120, a time ($T_0$) at which a data signal within a different predetermined range is expected to be generated at another collector (i.e., Channel0) spaced equidistantly from Channel1 is computed by subtracting the time difference from T1. As shown in block 122, a signal generated at Channel0 at time ($T_0$) is read. At block 124, a determination is made regarding whether the signal generated at Channel0 is valid (i.e., fits within a predetermined signal range for the calibration particle set for Channel0). Upon determining the signal is not valid, the process returns to block 102 to attempt to calibrate the flow cytometer again. On the contrary, if the signal generated at Channel0 is within acceptable limits confirming a time-of-flight calibration particle, variable dt_valid is set to 1 as shown in block 126. dt_valid is a Boolean variable that is 1 when dt is a calculated and has a valid value, while dt_valid is 0 when dt has not yet been calculated. For clarity purposes, the constants, variables, and processes used in the flow chart of FIG. 10 as well as FIG. 11 are defined further below.

Returning to FIG. 9, regardless of whether the identify of a calibration particle is verified through blocks 86-94 or if the process routes directly to block 96 from block 86, the methods and systems described herein may be configured to pinpoint other signal pulses received from each of the collectors and generated at distinct points in time in accordance with the calculated time-of-flight and relative positions of respective interrogation points corresponding to the collectors as shown in block 96. The other signal pulses are then associated to a particle of a different particle set as shown in block 98. Such a sequence of processes may alternatively be described as assigning a pulse on a channel of a first collector to a particular particle, identifying a pulse on a channel of a distinct second collector generated at a point in time in accordance with the time-of-flight and spacing between interrogation points of the flow cytometer corresponding to the first and second collectors, and assigning the pulse on the channel of the second collector to the particular particle. In addition, the methods and systems may further include identifying pulses on channels of one or more other collectors generated at points in time in accordance with the time-of-flight and spacing of interrogation points corresponding to the first, second, and one or more collectors and assigning the pulses on the channels of the one or more other collectors to the particular particle. As shown in FIG. 9, the process may be additionally routed back to block 96 to identify other signal pulses received from the collectors and assign such pulses to particles. In addition, the method may continue to block 99 to determine characteristics of the particle based on the associated signal pulses.

As noted above, it is believed in many cases particle velocities through a flow cytometer will vary enough to justify frequent recalibration. As such, the method may include recalibrating the flow cytometer using a different calibration particle flowing through the flow cytometer subsequent to the steps of assigning the associated signal pulses to a particular particle as denoted by the arrow connecting blocks 98 and 82. It is noted that such a recalibration process may be automatically initiated upon detection of a calibration particle by detecting two signal pulses that respectively fit within the predetermined signal ranges of the calibration particle set. Prior to such detection, several other sets of signal pulses may be identified and assigned to a particle. In other words, the processes outlined in blocks 96-99 may iteratively repeated until a calibration particle is detected.

FIG. 11 illustrates an exemplary flow chart for correlating pulses generated from multiple interrogation points to particular particles based on a calculated time-of-flight for the particles and the spacing of the interrogation points. It is noted that FIG. 11 is exemplary and, thus, other manners of carrying out the processes outlined in blocks 96 and 98 of FIG. 9 may be employed. For instance, FIG. 11 specifically calls for using the same time difference (dt) to correlate pulses generated at different interrogation points and, thus, assumes a flow cytometer configuration having evenly spaced interrogation regions. As noted above, however, interrogation points may alternatively be unevenly distributed in an interrogation zone and, therefore, the time difference used to correlate pulses may vary among interrogation points. Other variations to the instructions noted in FIG. 11 may be also or alternatively employed based on the discussions noted above. As shown in block 130 of FIG. 11, the process may include reading Boolean variable dt_valid established by the process outlined in FIG. 10. At block 132, a determination is made regarding whether dt_valid is equal to 1 and if it is not the process is routed to block 134 to run a dt_calculation process, such as the one described in reference to FIG. 10.

Upon determining dt_valid is equal to 1, the process routes to block 136 at which a valid signal pulse is detected (i.e., a pulse above a minimum threshold which is indicative that a particle from any of the subsets of particles within the assay being examined is at the interrogation point corresponding to Channel0). Thereafter, a time delay is incurred at block 138 such that current time t equals $T_0$+dt (i.e., the time the signal detected at Channel0 plus the time difference computed for the time-of-flight calculation of a calibration particle flowing through the flow cytometer). After the time delay, the signal at Channel1 is read as noted in block 140. At block 142, two determinations are made regarding the signal read at Channel1. In particular, a determination is made whether the signal is greater than or equal to "dt_calc_threshold" (i.e., the predetermined signal range associated with the calibration particle set specific to Channel1) or if the signal is less than a "min_detect" (i.e., minimum threshold which is indicative that at least one particle from any of the subsets of particles within the assay being examined is at the interrogation point corresponding to Channel1).

If either determination is made, the process may route back to block 134 to run a dt_calculation process and establish a new time-of-flight of a calibration particle and a corresponding dt to correlate pulses at multiple interrogation points to one particle. In particular, if the signal generated from Channel1 is greater than or equal to "dt_calc_threshold", such a signal may be indicative of a calibration particle or an agglomerate of particles and thus, recalibration of the flow cytometer may be desirable based on detecting such a signal. On the contrary, if the signal generated from Channel1 is less than min_detect, such a signal may be indicative that the time-of-flight of the particles in the flow cytometer has been altered relative to the time-of-flight determined for the most recent calibration particle passing through the interrogation zone and, thus, recalibration of the flow cytometer may be desirable. It is noted that instead of routing the process back to block 134 to recalibrate the flow cytometer after detecting either scenario presented in block 142, the method may alternatively return to block 136 in some embodiments and start the subprocess of detecting a valid signal on Channel0. In particular, it may be desirable to forego recalibrating the flow cytometer each time one of the scenarios presented in block 142 is detected. In some embodiments, the routing of the process may be selective based on the detection of the scenarios presented in block 142.

In any case, when neither scenario is detected in block 142, the process may continue to block 146 and read a signal generated at Channel2 after a time delay specified by block 144. As shown in blocks 148 and 150, such a process may be repeated n number of times, n being the number of interrogation points in the flow cytometer. In some cases, decision blocks may be incorporated into the process after reading signals at one or more of the channels to determine if the signals is equal to or greater than a min_detect for the respective channel as described for block 142. If the signal is less than min_detect, such a signal may be indicative that the time-off-light of the particles in the flow cytometer has been altered relative to the time-of-flight determined for the most recent calibration particle passing through the interrogation zone and, thus, recalibration of the flow cytometer may be desirable at such a point. Such additional processing is not shown in FIG. 11 to simplify the drawing, but the three connection dots between blocks 146 and 148 may infer such inclusion. For clarity purposes, the constants, variables, and processes used in the flow chart of FIG. 11 as well as FIG. 10 are defined further below.

It will be appreciated to those skilled in the art having the benefit of this disclosure that this invention is believed to provide methods, storage mediums, and systems for correlating pulses generated from multiple interrogation regions in a flow cytometer to particular particles flowing through the flow cytometer. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

DEFINITION OF VARIABLES, AND CONSTANTS

The constants and variables used in the flow charts of FIGS. 10 and 11 are as follows.
Channel0: This is a generic name for "DD."
Channel1: This is a generic name for "CL1."
Channel2: This is a generic name for "CL2."
Channeln: This is a generic name showing that the number of channels of detection is not limited.
Channel0_signal: This is a variable that is assigned the magnitude of the signal on Channel0.
Channel1_signal: This is a variable that is assigned the magnitude of the signal on Channel1.
Channel2_signal: This is a variable that is assigned the magnitude of the signal on Channel2.
min_delay: This is a constant containing a minimum delay between consecutive channel pulses. The use of this constant prevents detection of different calibration particles which may be flowing in succession between interrogation points.
dt: The microsphere travel time between interrogation points and therefore the time between pulses on consecutive channels.
dt_valid: Boolean variable where 1 means that dt has been determined with the "dt_calculation" process and 0 means that dt contains an unknown value and should not be trusted.
dt_calc_threshold: This is a constant value that sets the threshold value that the Channel1_signal and Channel2_signal must cross to be considered a calibration microsphere.
min_detect: Minimum threshold which is indicative that at least one particle from any of the subsets of particles within the assay being examined is at the interrogation point.
t: A variable containing the running time index.
$T_0$: A variable containing the time index of when Channel0_signal crosses the lower threshold.
$T_1$: A variable containing the time index of the Channel1 peak used in the process "dt_calculation."
$T_2$: A variable containing the time index of the Channel2 peak used in the process "dt_calculation."

DEFINITION OF PROCESSES

Listed here are processes used in the flow charts of FIGS. 10 and 11:
microsphere_peak_detect: The process that correlates signal pulses on multiple channels to create a microsphere detection event.
dt_calculation: The sub process that calculates dt and sets dt_valid to 1.
Channel0_peak_detect: The sub process that finds a valid signal pulse on Channel0.
Channel1_detect: The sub process that reads a signal on Channel1.
Channel2_detect: The sub process that reads a signal on Channel2.
Channeln_detect: The sub process that reads a signal on Channeln.

What is claimed:

1. A flow cytometer, comprising:
a particle flow path;
an illumination system configured to direct light toward multiple and distinct interrogation points of the particle flow path;
a plurality of collectors respectively configured to gather light from an interrogation region comprising the interrogation point and further configured to generate signals representative of a degree of light gathered; and
an examination system comprising a processor and program instructions executable by the processor for:
receiving said signals;
comparing received signals of at least two collectors to predetermined signal ranges associated with a specific particle set;
identifying a particle of the specific particle set upon detecting signal pulses that respectively fit within the predetermined signal ranges;
calculating a time-of-flight of the particle using a time difference between signal pulses received from the at least two collectors;
pinpointing other signal pulses received from each of the collectors and generated at distinct points in time in accordance with the calculated time-of-flight and relative positions of respective interrogation points corresponding to the collectors; and
associating the other signal pulses to a particle of a different particle set.

2. The flow cytometer of claim 1, wherein the examination system further comprises program instructions executable by the processor for determining characteristics of the particle of the different particle set based on the associated signal pulses.

3. The flow cytometer of claim 1, wherein the examination system further comprises program instructions executable by the processor for verifying, upon identifying a particle of the specific particle set, a data signal received from another collector is within a preset signal range, wherein the signal pulse received from the other collector is at a point in time in accordance with the calculated time of flight and a position of an interrogation point corresponding to the other collector relative to positions of the interrogation points corresponding to the two collectors.

4. The flow cytometer of claim 1, wherein distances between the multiple and distinct interrogation points are known, and wherein the examination system further comprises program instructions executable by the processor for determining a velocity of the particle.

5. The flow cytometer of claim 1, wherein the multiple and distinct interrogation points are evenly spaced along the particle flow path.

6. The flow cytometer of claim 1, wherein the multiple and distinct interrogation points are unevenly distributed along the particle flow path.

7. The flow cytometer of claim 1, wherein the two interrogation points corresponding to the two collectors are consecutively arranged along the particle flow path.

8. The flow cytometer of claim 1, wherein at least one interrogation point is interposed between the two interrogation points corresponding to the two collectors.

* * * * *